US007959810B1

(12) United States Patent
Dreux et al.

(10) Patent No.: US 7,959,810 B1
(45) Date of Patent: Jun. 14, 2011

(54) METHOD FOR ADAPTING A DETECTION DEVICE TO BE COUPLED TO A LIQUID CHROMATOGRAPHY COLUMN AND EQUIPPED WITH MEANS FOR FORMING AND CONVEYING AN AEROSOL

(75) Inventors: Michel Dreux, Olivet (FR); Davy Guillarme, Gaillard (FR); Jean-Luc Veuthey, Vessy (CH)

(73) Assignee: Societe d'Etdudes de Developpment et de Realisations Sedere, Alfortville (FR)

( * ) Notice: Subject to any disclaimer, the term of this patent is extended or adjusted under 35 U.S.C. 154(b) by 188 days.

(21) Appl. No.: 12/162,546

(22) PCT Filed: Jan. 22, 2007

(86) PCT No.: PCT/FR2007/050669

§ 371 (c)(1), (2), (4) Date: Jul. 29, 2008

(87) PCT Pub. No.: WO2007/088294

PCT Pub. Date: Aug. 9, 2007

(30) Foreign Application Priority Data

Feb. 2, 2006 (FR) .................................... 06 50372

(51) Int. Cl.
*B01D 15/08* (2006.01)

(52) U.S. Cl. ..................... 210/656; 210/198.2; 250/288; 250/289; 356/316

(58) Field of Classification Search .................. 210/656, 210/659, 198.2; 250/288, 289; 356/316
See application file for complete search history.

(56) References Cited

U.S. PATENT DOCUMENTS

| | | | | |
|---|---|---|---|---|
| 7,145,137 | B2 * | 12/2006 | Montaser et al. | 250/288 |
| 7,561,268 | B2 * | 7/2009 | O'Donohue et al. | 356/337 |
| 2001/0001575 | A1 | 5/2001 | Anderson, Jr. et al. | |
| 2003/0086092 | A1 | 5/2003 | Gangloff et al. | |
| 2005/0195393 | A1 * | 9/2005 | Karanassios | 356/316 |
| 2005/0224709 | A1 * | 10/2005 | Montaser et al. | 250/288 |
| 2005/0230617 | A1 * | 10/2005 | Montaser et al. | 250/288 |
| 2006/0285108 | A1 * | 12/2006 | Morrisroe | 356/316 |
| 2007/0299561 | A1 * | 12/2007 | Montaser et al. | 700/283 |

FOREIGN PATENT DOCUMENTS

| | | | |
|---|---|---|---|
| EP | 1275961 | A1 | 1/2003 |
| WO | WO2004/077047 | A1 | 9/2004 |

OTHER PUBLICATIONS

Anonymous: "Sedex LT-ELSD Model 75"[Online] May 31, 2005, p. i /i, XP002445215 Internet extract: URL:http://web.archive.org/web/20050310000 046/http://www.sedere.com/specs/spec75.htm i> [extracted Aug. 1, 2007].*

Anonymous "Internet Extract—Sedex LT-ELSD Model", May 31, 2005.

Anonymous "Internet Extract—ELSD Detektor fur Mikro-HPLC", Feb. 25, 2005.

Gaudin et al. "Adaptation of an evaporative light-scattering detector to micro and capillary liquid chromatography and response assessment" Journal of Chromatography, Elsevier Science Publishers B.V. Amsterdam, NL vol. 1051, No. 1-2 Oct. 8, 2004, pp. 43-51.

* cited by examiner

*Primary Examiner* — Ernest G Therkorn
(74) *Attorney, Agent, or Firm* — Baker & Daniels LLP

(57) ABSTRACT

The present invention relates to a method for adapting a detection device to be coupled to a liquid chromatography column and equipped with means for forming and conveying an aerosol as well as means for the formation of an aerosol and the conveyance thereof towards these detection means.

14 Claims, 4 Drawing Sheets

METHOD FOR ADAPTING A DETECTION DEVICE TO BE COUPLED TO A LIQUID CHROMATOGRAPHY COLUMN AND EQUIPPED WITH MEANS FOR FORMING AND CONVEYING AN AEROSOL

This application is a U.S. National Phase Patent Application based on International Application Serial No. PCT/FR2007/050669 filed Jan. 22, 2007, the disclosure of which is hereby explicitly incorporated by reference herein.

The present invention relates to a detector to be coupled to a liquid chromatography column and equipped with detection means as well as means for the formation of an aerosol and the conveyance thereof towards these detection means.

The means for forming an aerosol by a detector of this type substantially include a nebulizer into which is introduced, on the one hand, a sample formed from a mobile phase involving the compounds to be analyzed which have been dissolved therein and, on the other hand, a nebulization gas.

The means for conveying the aerosol are substantially formed from an evaporation chamber which is generally a heated tube in which the mobile phase is evaporated in order to retain only the microparticles of the compounds to be analyzed.

It should be noted that the intermediate phase of the transformation from liquid, which exits the chromatography column, into an aerosol is almost obligatory, since an aerosol is easier to transport and evaporate than a liquid.

Separation methods and, in particular, liquid chromatography have been producing a plurality of growth axes for several years.

Standard chromatography, for which columns having an internal diameter of approximately 4 mm and high flow rates of approximately 1000 μl/mn are used, is increasingly being replaced, in particular by microchromatography, for which flow rates of approximately 200 μl/mn are used, even capillary chromatography for which flow rates are approximately 4 μl/mn and even nano chromatography for which flow rates are less than 1 μl/mn.

During implementation of these techniques, the diameter of the column must naturally be reduced in consequence thereof.

This miniaturisation has many advantages, among which is, in particular, the decrease in the quantity of organic solvents used with regard to the lower flow rates.

Moreover, the lower the flow rate of the carrier liquid (the mobile phase), the higher the concentration of the product to be detected, according to the theory of chromatography.

Conventionally the use of low flow rates should therefore be advantageous.

This situation is illustrated by the conventional table below.

TABLE 1

| Internal diameter of the column (mm) | Mobile phase flow rate (μl/Min) | Concentration at column exit if quantity injected is identical (C) | Signal gain |
|---|---|---|---|
| 4.6 | 1000 | C | 1 |
| 3 | 450 | 2.35 × C | 2 |
| 2.1 | 200 | 5 × C | 5 |
| 1 | 50 | 21 × C | 20 |
| 0.5 | 10 | 85 × C | 80 |
| 0.3 | 4 | 235 × C | 230 |

This table shows that if, for a column having an internal diameter of 4.6 mm and a mobile phase flow rate of 1000 μl/mn, a concentration C of compounds to be analyzed may be detected at the exit of the column, a concentration 235 times greater than these compounds may be detected using a column having an internal diameter of 0.3 mm and a mobile phase flow rate of 4 μl/mn This means that if the same quantity of compounds to be analyzed were injected, the smaller the internal diameter of the column and the lower the mobile phase flow rate, the higher the chromatographic peaks, and therefore the easier these compounds are to detect.

In other words, Table 1 shows that in chromatography columns with small diameters and for low mobile phase flow rates, even weaker concentrations may be detected.

However, in addition to this notion of sensitivity, the notion of chromatographic efficiency must be taken into account, this consisting of different parameters, including the width of a chromatographic peak at mid-height (W½) or the number N of theoretical plates which may be obtained or the number H corresponding to the same height as a theoretical plate.

These parameters are indicative of the quality of chromatography.

DESCRIPTION OF THE PREFERRED EMBODIMENTS

Figure 1:
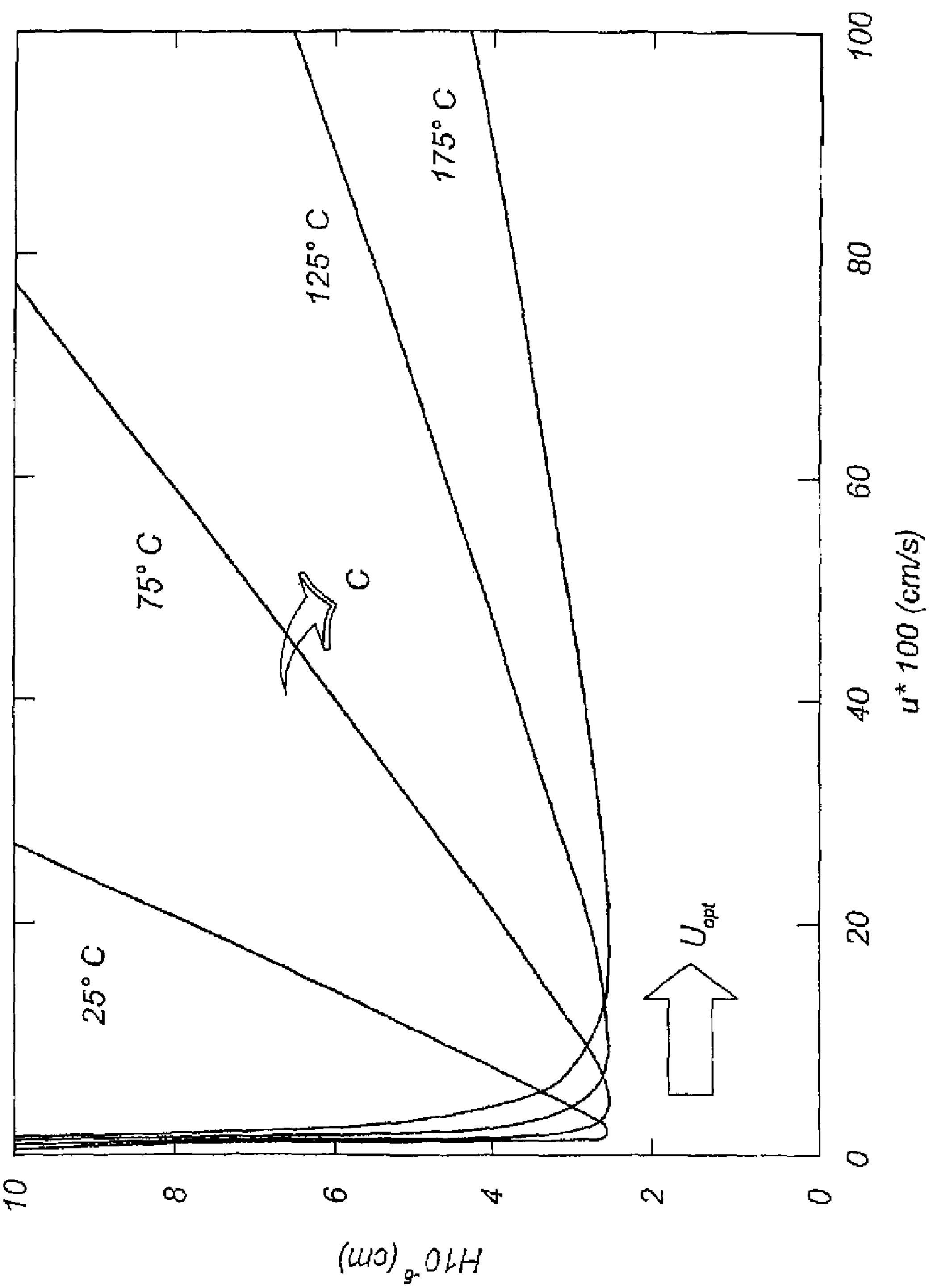
FIG. 1 shows the variations in chromatographic efficiency expressed by the height equivalent to a theoretical plate H as a function of the linear velocity u of the mobile phase in the column for 4 different temperatures (25° C., 75° C., 125° C., 175° C.).

FIG. 1 shows the variations in chromatographic efficiency expressed by the height equivalent to a theoretical plate H as a function of the linear velocity u of the mobile phase in the column for 4 different temperatures (25° C., 75° C., 125° C., 175° C.).

It should be noted that it is always advantageous to work closely to the smallest of these curves, given that the smaller the height equivalent to a theoretical plate H, the better the efficiency N.

The curve for 25° C. shows that efficiency decreases very sharply with the linear velocity of the mobile phase in the column.

On the other hand, as regards the curve for 175° C., this efficiency varies only very slightly when the linear velocity of the mobile phase increases.

Therefore, at this temperature, work may be carried out three to five times more quickly by maintaining the same efficiency, whereas at a low temperature, if the velocity is increased, the efficiency of the separation is immediately reduced.

In conclusion, the curves in FIG. 1 demonstrate the benefit of high-speed, high-temperature chromatography.

However, it is essential that the performances, in particular the efficiency obtained at the exit of the column, be retained whilst the sample in the detector, which is coupled to this column, is conveyed to the detection means, thereby precluding chromatographic peak broadening at this level.

Optimising these detectors is therefore necessary.

At present, on the market there are a large range of detectors of the above-mentioned type to be coupled to a liquid chromatography column in which the detection means may be optical, electrical or otherwise.

The different types of detection are often differentiated by the transformation of the compounds to be analyzed which, in the solution in the aerosol droplets, are encountered in the gas phase after evaporation, for example in the form of particles, as is the case with the evaporative light scattering detector or ELSD in the form of particles, the size of which has been increased by nucleation using a suitable reactant, as is the case with the condensation nucleation light scattering detector or CNLSD in the form of particles of electrically charged solutes, as is the case with the charged aerosol detector or CAD or even in the form of ions, as is the case with the Mass Spectrometry or MS detector or the chemiLuminescent nitrogen detector or CNLD When coupled to the liquid or supercritical fluid chromatography (SFC) columns or other means of liquid separation (counter current chromatography or CCC), the performance of these detectors varies considerably; however, nearly all operate better with lower mobile phase flow rates than with higher flow rates, and some, such as the MS and the CLND, are even incompatible with flow rates of 1 ml/mn.

Taking account the foregoing, it would advantageous to adapt these detectors so as to be able to carry out quick analyses at high temperatures without adversely affecting chromatographic efficiency.

However, in standard chromatography, it is impossible nowadays to increase the linear velocity of the mobile phase whilst operating at a high temperature, since excessively high pressures would be obtained, thus leading to a rapid degradation of the apparatus.

The occurrences of peak broadening which are more often than not insignificant in analytical flow rates on a standard chromatography column (with an internal diameter of 4.6 mm and flow rate of 1 ml/mn) become unacceptable when the mobile phase flow rate in columns with smaller diameters is reduced.

In this context, the present invention relates to adapting detectors of the above-mentioned type, which are to be coupled to a liquid chromatography column, to high-temperature, quick microchromatography whilst optimising them so as to eliminate or at least reduce the occurrences of peak broadening, and therefore loss of chromatographic efficiency, whilst the sample is conveyed between the exit of the chromatographic column and the detection means.

According to the invention, the main origin of these occurrences could be determined by carrying out tests on specific detectors, namely ELSDs marketed by SEDERE under the name SEDEX.

Detectors of this type are equipped with a spray chamber which is connected to the nebulizer and mounted upstream of the evaporation chamber.

The nebulizer is a concentric nebulizer of the Venturi type in which the nebulization gas arrives tangentially via a concentric nozzle, so as to coaxially envelop the sample flow to be analyzed.

The spray chamber is used as a filter to allow the aerosol droplets formed in the nebulizer to be narrowly dispersed across the diameter; in fact, the largest droplets which are located outside the jet and are slower than the smaller droplets in the median part thereof are eliminated through condensation on the walls of the spray chamber then evacuated and eliminated using a water seal; consequently, the central part of the jet is practically the only part to be conveyed towards the evaporation chamber via a median orifice.

In practice, it is essential to not convey the entire sample exiting the chromatography column towards the detection means which would otherwise be very quickly polluted, since the largest aerosol droplets must be eliminated because they are more difficult to evaporate. These aerosol droplets are detrimental to the signal-noise ratio, since they increase the background noise.

In the SEDEX detectors, the spray chamber forms with the nebulizer an assembly which may be removed, mounted and dismounted in only several minutes and which is completely accessible, in such a way that it allows the apparatus to be optimised as a function of the type of chromatography.

At present, these detectors may therefore be equipped with three different spray chambers which may be changed very easily and very quickly, depending on the requirements and models, namely a conventional spray chamber, a standard double-wall spray chamber suitable for supercritical chromatography and a spray chamber suitable for combinatorial chemistry.

A plurality of nebulizers may fit these spray chambers in order to be adapted to the most diverse flow rates (5 μl/mn to 5 ml/mn), so as to optimise the signal-noise ratio which depends heavily on the mobile phase flow rate.

It should be noted that apart from mass spectrometry, no other detectors of the above-mentioned type at present on the market are equipped with a similar spray chamber.

In these detectors, the largest aerosol droplets formed by the nebulizer are generally also eliminated, but in another "frozen" part of the apparatus which is neither visible nor accessible without being modified.

More specifically, this is the case for all ELSD manufacturers but also for the other types of detection which are equipped with filters presented under the names "Impactor" (ELSD), "diffuser" (ELSD), diffusion filter (CNLSD) and mass filter (MS, CAD).

The observed occurrences of chromatographic peak broadening may only be located mainly downstream of the nebulizers which are almost always of the pneumatic type and may have physical features which are relatively different, depending on the manufacturers.

Specifically, optimisation through nebulization is generally carried out using conventional parameters which constitute gas and liquid flow rates.

Some manufacturers even use the heating of the nebulizer as an additional parameter.

According to the invention, it could be established that in the SEDEX ELSD, the loss of efficiency substantially occurs in the spray chamber, the shape of which is unsuitable for low mobile phase flow rates and therefore for microchromatography.

Tests carried out on a modified detector without a spray chamber have in fact clearly demonstrated that a significant decrease in the adverse extra-column effects can thus be obtained.

The object of the invention is therefore to propose a detector to be coupled to a liquid chromatography column which is capable of being adapted to all types of chromatography, in particular to high-speed, high-temperature microchromatography, which allows a faithful image of the chromatographic efficiency to be translated into the efficiency of the peaks that it delivers.

According to the invention, a detector of this type which comprises detection means as well as means for forming an aerosol, comprising a nebulizer and means for conveying this aerosol towards the detection means, is characterised in that the means for conveying the aerosol towards the detection means comprises at least two removable spray chambers which are substantially cylindrical and connected to the nebulizer, namely a standard spray chamber suitable for conventional chromatography and a modified spray chamber with a shape suitable for high-speed, high-temperature microchromatography.

A detector of this type may advantageously be formed from an ELSD but may also correspond, without departing from the scope of the invention, to any detector located downstream of a liquid chromatography column, including nebulization stages, i.e. transformation into an aerosol in the mobile phase exiting the chromatography column, vaporisation of this aerosol and detection thereof.

It should be noted that a modified spray chamber suitable for microchromatography cannot be used above specific flow rates, since, due to turbulence, the results cannot be reproduced.

It is therefore essential that the detector according to the invention can have, depending on the type of chromatography, a plurality of different spray chambers which can be changed easily and quickly, depending on what is required.

The modified spray chamber must naturally generally act as a filtration means which allows the largest aerosol droplets to be eliminated so that the droplets conveyed towards the detection means can be narrowly dispersed.

In practice, this filtration means can eliminate up to approximately 80% of the sample exiting the chromatography column.

According to the invention, different physical and geometrical parameters of the spray chamber have been studied in order to influence the peak broadening and loss of efficiency relative to the chromatographic efficiency.

It has thus been possible to establish that the most influential parameters are the diameter of the spray chamber, the length of this chamber as well as the curvature thereof, i.e. the angle of the path of the aerosol droplets between the entrance and the exit of this chamber.

Therefore, according to another feature of the invention, the diameter of the modified spray chamber is smaller than the diameter of the standard spray chamber.

Therefore, the modified spray chamber can advantageously be approximately twice as narrow as the standard spray chamber.

According to another feature of the invention, the modified spray chamber is shorter than the standard spray chamber, the modified spray chamber can thus advantageously be approximately twice as short as the standard spray chamber.

According to another feature of the invention, the shape of the modified spray chamber is chosen in such a way that the path of the aerosol droplets between the entrance and the exit of this chamber form an angle of approximately 90°.

An angle of this type corresponds in fact to that of the path of the aerosol droplets in the standard spray chamber.

According to a particularly advantageous feature of the invention, the shape of the modified spray chamber is chosen in such a way that the path of the aerosol droplets between the entrance and the exit of this chamber forms an angle of approximately 120°.

To ascertain the advantages of the detector according to the invention, tests were carried out from an ELSD detector marketed by SEDERE under the name of SEDEX 85 which was equipped with different modified or unmodified spray chambers and used in adverse chromatographic conditions in order to be able to best visualise the differences between the different spray chambers (miniaturised system—microchromatography, a low retention factor k (equal to 2) and finally a flow rate three times greater than that conventionally used (high-speed chromatography)).

A 15-cm column has also been used as a model, 5 μm theoretically being required to yield 15000 plates.

The configuration of the spray chambers thus tested was as follows:

- standard configuration: original spray chamber with no modification,
- narrow configuration, 90°: custom-fitting spray chamber which is twice as narrow as the standard spray chamber, the angle of curvature of this chamber being kept at 90°,
- narrow, short configuration, 90°: custom-fitting spray chamber which is twice as narrow and twice as short as the standard spray chamber, the angle of curvature of this chamber being kept at 90°,
- narrow, short configuration, 120°: custom-fitting spray chamber which is twice as narrow and twice as short as the standard spray chamber, the curvature of this spray chamber having been modified to be equal to 120°,
- configuration without spray chamber.

A test was also carried out with the spray chamber with the narrow, short, 120° configuration while increasing the spray pressure from 3 to 5 bars.

Figure 2:
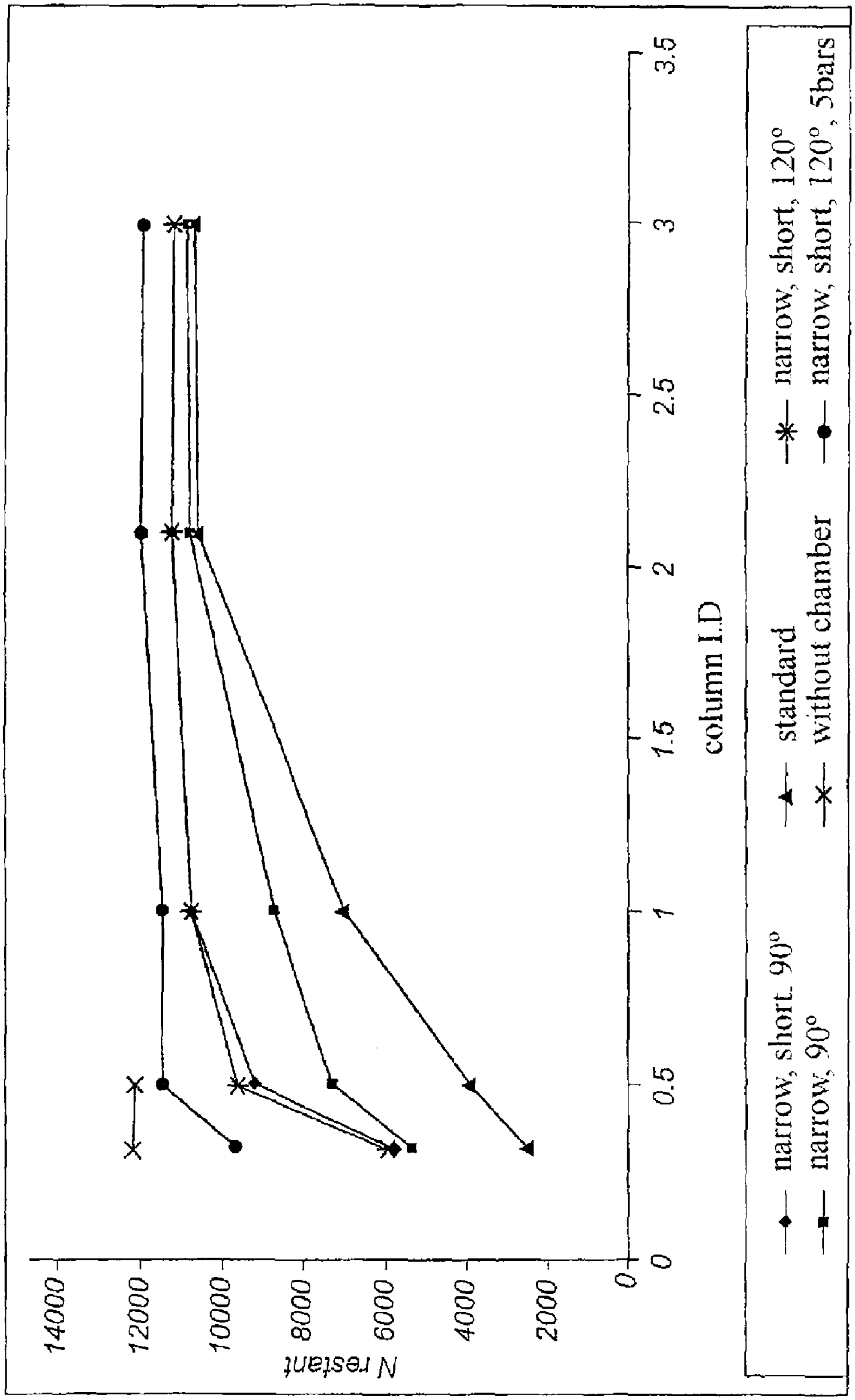
FIG. 2 shows the number variation in the remaining theoretical plates N, for each of the tested spray chambers, as a function of the internal diameter (I.D.) of the column.

FIG. 2 shows the number variation in the remaining theoretical plates N, for each of the tested spray chambers, as a function of the internal diameter (I.D.) of the column.

This figure shows that:

- the standard spray chamber makes it possible to operate with a limited loss of efficiency for standard columns with an internal diameter (I.D.) of between 2.1 and 4.6 mm but is incompatible with the smallest columns (I.D. ≦ to 1 mm) when work is carried out at high velocity (N=3800 with a column having a diameter of 500 μm),
- reducing the diameter of the spray chamber (narrow configuration, 90°) allows the loss in efficiency in high-speed microchromatography (N=7000 with a column having a diameter of 500 μm) to be substantially reduced,
- simultaneously reducing the diameter and the length of the spray chamber (narrow, short configuration, 90°) allows the results in high-speed microchromatography (N=9500 with a column having a diameter of 500 μm) to be greatly improved,
- modifying the angle of curvature of the spray chamber (narrow, short configuration, 120°) appears to have only a slight influence on the efficiency (N=9800 with a column having a diameter of 500 μm),
- increasing the spray pressure from 3 to 5 bars (narrow, short configuration, 120°, 5 bars) markedly improves the quality of the chromatographic peak (N=11800 with a column having a diameter of 500 μm),
- finally, without a spray chamber, the efficiency obtained (N=12200 with a column having a diameter of 500 μm) is the same as that obtained with the best spray chamber (narrow, short configuration, 120°, 5 bars).

The test thus carried out therefore shows that the spray chamber with the narrow, short, 120° configuration seems the most appropriate to retain a sufficient efficiency with a microchromatography assembly and a fortiori with a high-speed microchromatography assembly.

To confirm the superiority of a spray chamber thus modified, additional tests were carried out in order to ensure that the gain in efficiency thus obtained relative to the standard spray chamber had not been detrimental to the sensitivity, as in the case of the configuration without a spray chamber.

Figure 3:
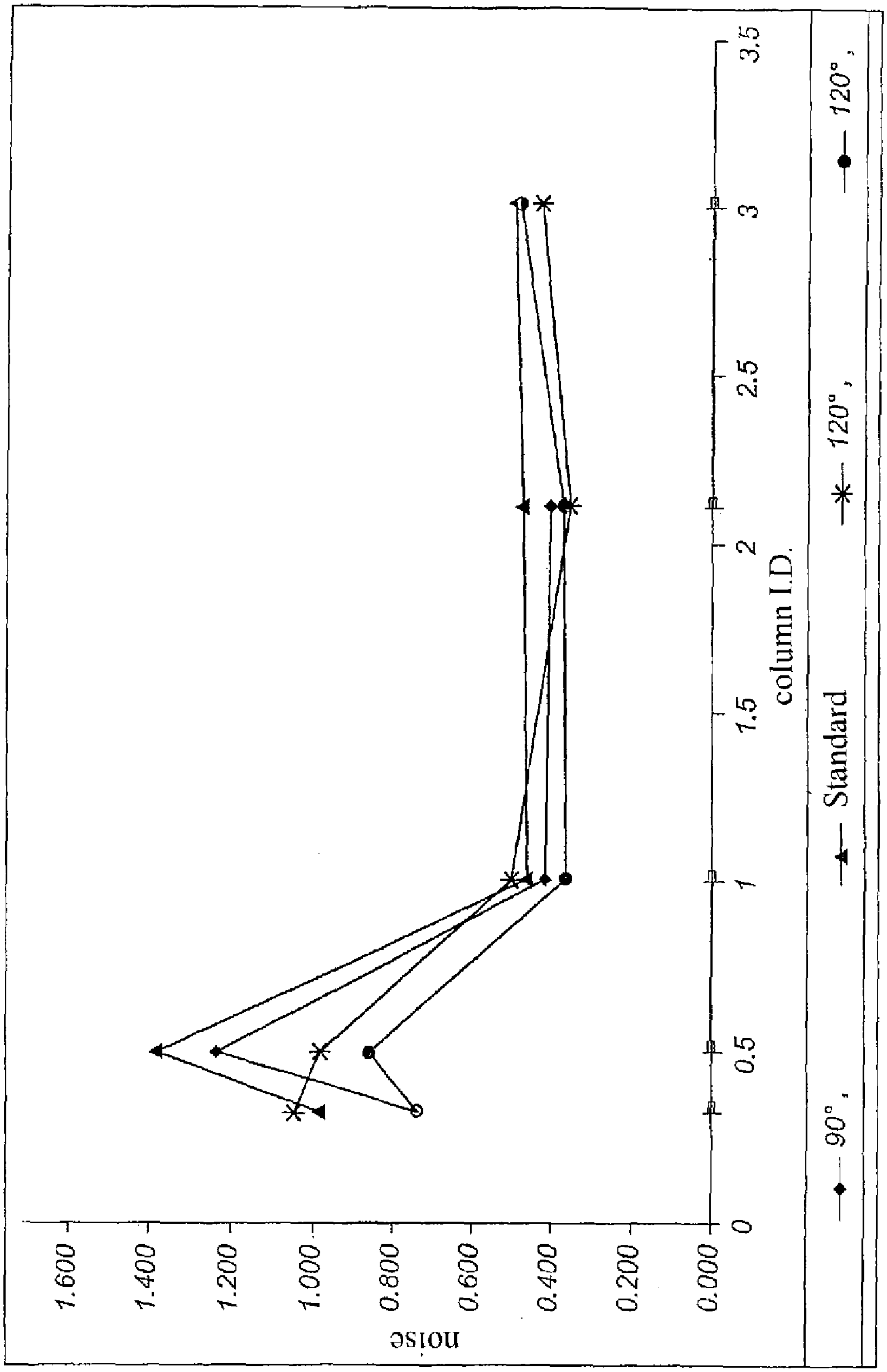
FIGS. 3 and 4 show, for the standard spray chamber and the modified spray chambers with narrow, short 90° and narrow, short, 120° configurations the variations in chromatographic noise and height of the chromatographic peak ((Height) mV) respectively, as a function of the internal diameter (I.D.) of the column, in the case of a quick chromatographic flow rate, i.e., equal to three times the standard flow rate.
Figure 4:
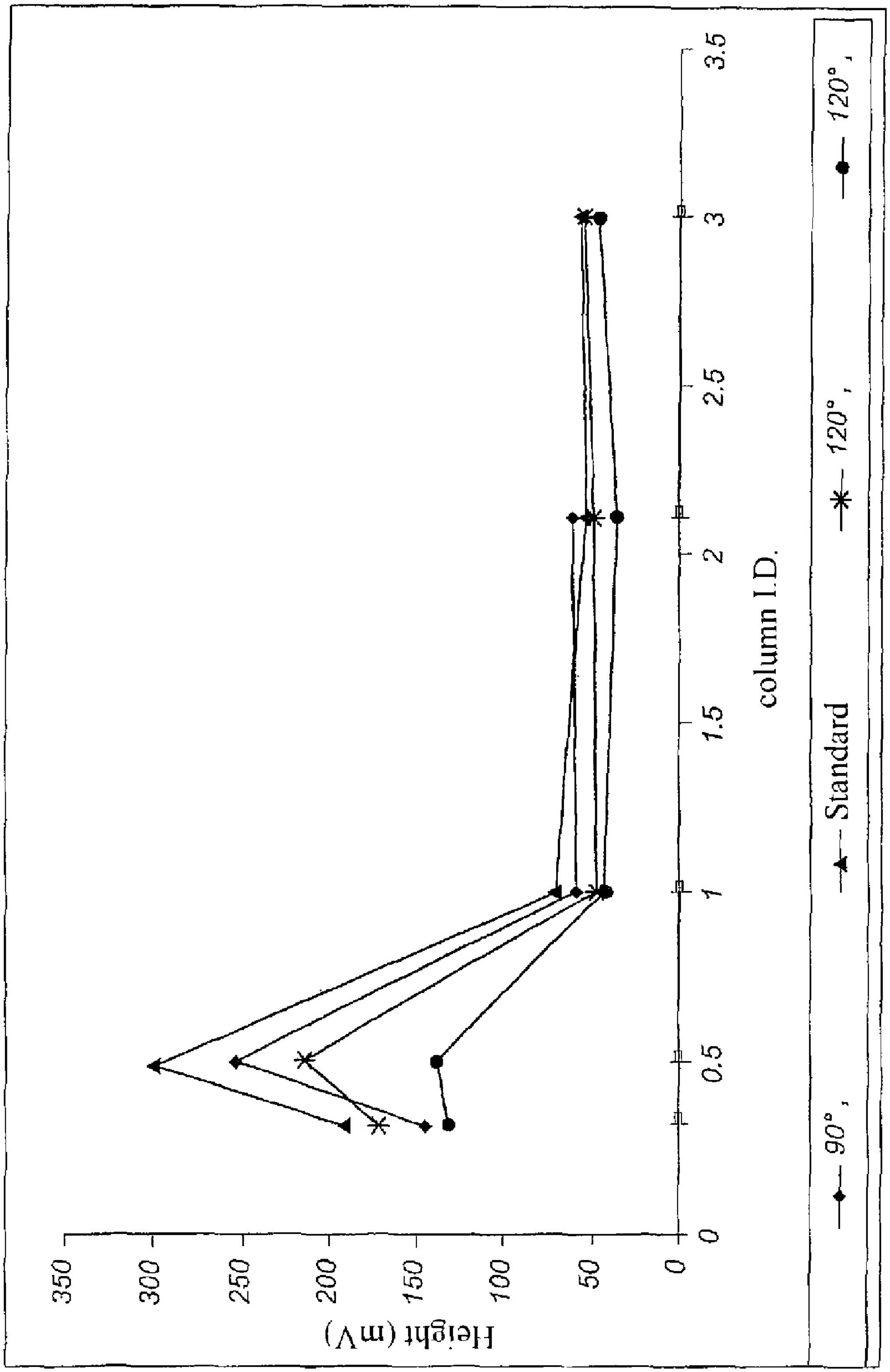

FIGS. 3 and 4 show, for the standard spray chamber and the modified spray chambers with narrow, short 90° and narrow, short, 120° configurations the variations in chromatographic noise and height of the chromatographic peak ((Height) mV) respectively, as a function of the internal diameter (I.D.) of the column, in the case of a quick chromatographic flow rate, i.e. equal to three times the standard flow rate.

These figures show that in every case the standard spray chamber provides the most intense signal but also the highest background noise.

The modified spray chambers allow the background noise to be reduced but also lead to a decrease in the signal.

Overall, in terms of signal-noise ratio, this signal-noise ratio does not vary substantially with the shape of the spray chamber and the sensitivity is the same between the standard spray chamber and the modified spray chamber with a narrow, short, 120° configuration.

These tests have therefore demonstrated that the modified spray chamber with a narrow, short, 120° configuration allows the losses in efficiency of the chromatographic peak in microchromatography or quick microchromatography to be reduced, and does not generate any substantial loss in sensitivity relative to a standard spray chamber.

On the other hand, this modified spray chamber does not provide any notable advantage for flow rates higher than 200 µl/mn to which the standard spray chamber is perfectly suited.

The above-mentioned tests have also demonstrated that the spray pressure plays a not insignificant role in the efficiency measured via the detection means, the residual efficiency being higher, the higher the pressure (or the flow rate) of the nebulization gas.

This increase in efficiency with the flow rate of nebulization gas can be interpreted from the fact that the speed of transfer towards the detection means of the compounds to be analyzed increases.

In the current detectors, this speed of transfer depends entirely on the gas flow rate imposed by the nebulization and cannot be modified at will.

To remedy this drawback, the idea according to the invention was to disassociate the two distinct stages of forming the aerosol and conveying the compounds to be analyzed towards the detection means.

For this purpose, according to a particularly advantageous feature of the invention, the modified spray chamber is equipped at the exit thereof with means which allow a flow of additional gas to be injected into the aerosol.

According to another feature of the invention, the modified spray chamber comprises a narrowing at the exit thereof and the additional gas flow is an annular flow injected into the aerosol at this level.

To prove the advantageous feature of such an injection of additional gas, tests were carried out on an ELSD marketed by SEDERE under the name SEDEX 75, whilst modifying the shape of the spray chamber of a detector of this type.

In this detector, the evaporation tube penetrates into the spray chamber at the exit of this chamber.

During these tests, the standard spray chamber was shrunk at the exit thereof in such a way that it could penetrate the evaporation tube at this level, and an additional airflow was injected into the aerosol through the hole thus created around the shrunk portion of the spray chamber.

The features of the chromatographic peak of glucose were then analyzed in succession with a standard detector and a detector thus modified in which different additional airflows were injected through the above-mentioned annular hole, under the following chromatographic conditions:

Kromasil C18 column, 50×4 mm, 5 µm, 1 ml/mn water, 20 µA glucose 5 ppm, Sedex 75 detector (3.5 bars, 50° C., gain 12), 150 µm nebulizer (1.74 l/mn).

The results thus obtained are collated in Table 2 below.

TABLE 2

| | Standard spray | Spray chamber with additional air (L/mn) | | | | |
|---|---|---|---|---|---|---|
| | chamber | 0 | 0.3 | 0.65 | 1 | 1.85 |
| Height (mV) | 92 | 109 | 105 | 98 | 91 | 72 |
| Peak width (W½ in s) | 3.66 | 3.87 | 3.43 | 3.09 | 2.98 | 2.62 |
| Symmetry (As) | 2.09 | 2.05 | 2.05 | 2.06 | 2.01 | 1.65 |

This table unequivocally explains the benefit of independently optimising the flow rate of nebulization gas which allows the aerosol to form and the gas flow rate which allows the transfer thereof towards the detection means in order to reduce the loss of chromatographic efficiency.

It should be noted that in the case of the modified spray chamber, if additional air is not injected, the flow coming from the spray chamber is first compressed then dilated, which is detrimental to the efficiency relative to the standard spray chamber.

In contrast, the height of the signal is greater which shows that the amount of aerosol sent towards the detection means increases with compression in the spray chamber since more product exits than in the absence of compression.

The addition of an extra airflow as a supplement to the gas required for the nebulization process may possibly increase the speed of transfer of the aerosol towards the optical detection means, thereby reducing the losses in chromatographic efficiency by decreasing the diffusion of the solutes during this accelerated transfer. An adverse effect of the decrease in the light signal broadcast by the solutes is noted and the decrease is all the more significant when the quantity of additional air is great.

It is seen, for example, that a flow rate as low as 0.65 l/mn of additional air added to the flow rate of 1.74 l/mn of the nebulizer allows the W½ to be decreased by more than 15% whilst increasing the height of the signal by 6%.

If the user wishes to improve the intensity of the signal, the efficiency or the symmetry of the peaks, he can consequently choose the added additional air flow.

These variations which are already easily observed with flow rates of 1 ml/mn would in theory be more substantial at a low flow rate and the addition of an additional gas flow into the aerosol is therefore somewhat beneficial.

It should be noted that according to the invention, fitting the standard spray chamber, as well as the modified spray chamber with a narrowing can also be considered, which would make it possible to increase the compression of the aerosol to be transported towards the detection means.

The invention claimed is:

1. A method for selectively adapting a detector to be coupled to a liquid chromatography column to facilitate production of an image of chromatographic efficiency, said method comprising the steps of:

providing an apparatus, comprising:

a liquid chromatography column including an entry end and an exit end, a nebulizer releasably connected to the exit end and operable to form aerosol droplets from a liquid exiting the exit end, a modified spray chamber in communication with the nebulizer and having a shape adapted for microchromatography, wherein the diameter of the modified spray chamber is smaller than the diameter of a standard spray chamber, wherein the modified spray chamber is configured to obtain a narrow size distribution of aerosol droplets conveyed towards the detector by eliminating the aerosol droplets of largest size, and wherein the nebulizer and the modified spray chamber form a detachable and accessible assembly which can be quickly mounted and dismounted from the liquid chromatography column, and a detector to receive the selected aerosol droplets from the standard spray chamber and the modified spray chamber, attaching the nebulizer and the modified spray chamber to the exit end of the liquid chromatography column;

preparing a sample with one or more compounds to be analyzed and one or more compounds forming a mobile phase;

loading the sample into the entry end of the liquid chromatography column;

transforming the sample into an aerosol as the sample exits the exit end of the column;

filtering the aerosol through the standard spray chamber and the modified spray chamber towards the detector; and detecting compounds present in the aerosol using the detector.

2. The method according to claim 1, characterized in that the modified spray chamber is approximately less than half of the diameter of the standard spray chamber.

3. The method according to claim 1 characterized in that the modified spray chamber includes a cylindrical axis and the standard spray chamber includes a cylindrical axis, and the length of the cylindrical axis of the modified spray chamber is smaller than the length of the cylindrical axis of the standard spray chamber.

4. The method according to claim 3, characterized in that the length of the cylindrical axis of the modified spray chamber is approximately half as long as the length of the cylindrical axis of the standard spray chamber.

5. The method according to claim 1, characterized in that the shape of the modified spray chamber is chosen in such a way that the path of the aerosol droplets between the exit of the modified spray chamber forms an angle of approximately 90°.

6. The method according to claim 1, characterized in that the shape of the modified spray chamber is chosen in such a way that the path of the aerosol droplets between the entrance and the exit of this chamber forms an angle of approximately 120°.

7. The method according to claim 1, characterized in that the modified spray chamber is equipped at the exit thereof with means for injecting an additional gas flow into the aerosol.

8. The method according to claim 7, characterized in that the modified spray chamber comprises a narrowing at the exit thereof and the additional gas flow is an annular flow injected into the aerosol at this level.

9. The method according to claim 1, characterized in that the standard spray chamber comprises a narrowing at the exit thereof.

10. The method of claim 1, further comprising an evaporation chamber between the modified spray chamber and the detector.

11. The method of claim 1, wherein the detector is an evaporative light scattering detector (ELSD).

12. The method of claim 1, wherein the geometry of the modified spray chamber is changed according to the type of detector used.

13. The method of claim 1, wherein the modified spray chamber allows saving more than 80% of the chromatographic efficiency before the sample travels to the detector.

14. The method of claim 1, wherein the flow rate of the mobile phase through the liquid chromatography column is 200 μl/min or less.

* * * * *